US00PP24483P3

(12) United States Plant Patent
Villegas

(10) Patent No.: US PP24,483 P3
(45) Date of Patent: May 20, 2014

(54) ***SANSEVIERIA* PLANT NAMED 'TWISTER'**

(50) Latin Name: *Sansevieria trifasciata*
Varietal Denomination: Twister

(75) Inventor: Marvin Gonzalez Villegas, San Ramon (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 13/374,902

(22) Filed: Jan. 23, 2012

(65) Prior Publication Data

US 2013/0191952 P1 Jul. 25, 2013

(51) Int. Cl.
*A01H 5/00* (2006.01)

(52) U.S. Cl.
USPC ..... Plt./382

(58) Field of Classification Search
USPC ..... Plt./382, 263.1, 226
See application file for complete search history.

*Primary Examiner* — Kent L Bell
(74) *Attorney, Agent, or Firm* — Foley & Lardner LLP

(57) ABSTRACT

The new variety 'Twister' is part of the "compact *Sansevieria* group". It can reach 45 cm in length, with an average of approximately seven leaves per plant. The plant shows an inverted pyramid shape and swirl, the arrangement of the leaves is in the form of a rosette. Shows very similar colors to the comparison variety 'Laurentii', with irregular margins showing variegated coloration, with alternating brilliant yellowish green (RHS 154B) and light yellowish green (154D RHS) horizontal bands. 'Twister' presents more leaves per rosette than the parent variety 'Black Gold Superba' and is more similar to the commercial variety 'Laurentii'.

3 Drawing Sheets

Latin name of the genus and species of the claimed plant: *Sansevieria trifasciata.*

Variety denomination: 'Twister'.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Twister'.

*Sansevieria* is a monocotyledonous and succulent, flowering plant which can be produced in either hard-leafed or soft-leafed varieties for interior use as a house plant or outdoor ornamental plant.

The new *Sansevieria* 'Twister' was discovered and selected by Mr. Marvin Gonzalez Villegas, as a single flowering plant within a planting of 'Black Gold Superba' at Monterrey, San Carlos, Alajuela province, Costa Rica in 2004. It originated as a naturally-occurring mutation of the *Sansevieria* variety 'Black Gold Superba' (unpatented).

Asexual reproduction of the new *Sansevieria* cultivar by vegetative cuttings was first performed in November 2004 in Monterrey, San Carlos, Alajuela, Costa Rica, and demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Twister', which in combination distinguish this *Sansevieria* as a new and distinct cultivar:

1. Variegated foliage with different green tones on the irregular bands, and yellowish green colored margin bands in the leaf blade.
2. Wide and lanceolate leaves, 45 cm long, supported in a rosette.
3. 35-45 cm plant height.
4. Erect plant habit.
5. Needs little water and is moderately drought tolerant.

The new variety 'Twister' is considered a variety of *Sansevieria* in the group denominated as "compact *Sansevieria* plants". The new variety presents an average of 7 leaves per plant when it reaches its maturity (between 8-10 months). The new variety has an erect growth habit and the entire plant can reach a height range between 35 and 45 cm. The leaves are narrow (5.5 cm average measured at the widest part of the mature leaf) and lanceolate with a soft, waxy texture. The blades are thin and slightly wavy. This variety also has an inverted triangle shape like the other *Sansevierias* of the compact group, but 'Twister' also has a swirl shape. The new variety is moderately drought tolerant and adapts well to conditions of light and shade (interior and exterior).

The leaves show a variegated coloration, with horizontal and alternate bands. In immature leaves these bands have a very pale green (RHS 130D) and deep yellowish-green coloration (141A RHS). The band coloration in the mature leaves becomes moderate yellowish-green (RHS 149B and 149D) within the same deep yellowish green (141A RHS) coloration.

The leaves have margins on both sides of the blade with an average width of 1.5 cm. The margins, which are irregular, show variegated coloration, with alternating brilliant yellowish green (RHS 154B) and light yellowish green (154D RHS) horizontal bands. The leaf blades are deep yellowish green (RHS 141A) colored in the surface of the leaf and also present non-uniform horizontal variegated bands of yellow-green (RHS 149D and RHS 149B) on both sides of some leaves.

Plants of the new *Sansevieria* 'Twister' differ from plants of the parental cultivar 'Black Gold Superba' (unpatented) in the characteristics described in Table 1.

The variety 'Black Gold Superba' gave rise to the var. 'Twister'. The 'Black Gold Superba' variety is also considered part of the "compact *Sansevieria* group". 'Black Gold Superba' shows less vigor than 'Twister', has fewer leaves per plant (3-4), with an average leaf width of 6.5 cm (measured in the middle of the mature leaf.) The growth habit is erect and presents wide leaves supported in a rosette. The entire plant can reach a size between 30-40 cm. The plant has, as for 'Twister', an inverted triangle shape. The leaves are lanceolate with a soft, waxy texture. The younger leaves show a yellowish green vivid coloration (RHS 134A) in the interior of the leaf blade. This area shows also irregular streaks or yellowish-green bands (RHS 142D) and there are margins in both sides of the leaf which are variegated with irregular horizontal bands that alternate between light yellowish green (RHS 142D) broad bands and brilliant yellowish green (RHS 149A) thin bands. When the leaf is mature the deep color inside turns yellowish green (RHS 141B), while margins alternate vivid greenish yellow (RHS 2A) and light-yellowish green (RHS 2C) colors.

TABLE 1

Comparison with Parental Variety

| Characteristic | New Cultivar 'Twister' | Female Parent 'Black Gold Superba' (unpatented) |
|---|---|---|
| Plant Vigor | more vigorous (more leaves) | less vigorous (less leaves) |
| Color | Variegated Foliage with different green tones on the irregular bands, and yellowish green colored margin bands in the leaf blade. | green leaves with yellow margins. |
| Shape | wide and lanceolate leaves on a rosette, swirl shape | wide and lanceolate leaves |
| Texture of leaves | smooth-textured leaves | smooth-textured leaves |

Of the many commercial cultivars known to the present inventor, the most similar in comparison to the new *Sansevieria* 'Twister' characteristics is the *Sansevieria* 'Laurentii' (unpatented), described in Table 2.

The variety 'Laurentii' does not belong to the "compact *Sansevieria* group", but is considered to be part of the "long leaf *Sansevieria* group". 'Laurentii' shows more vigor with a height ranging between 35-64 cm. 'Laurentii' produces 2-4 leaves per plant with an average leaf width of 6 cm (measured in the middle of the mature leaf.).

'Laurentii' shows a coloration very similar to the new variety 'Twister', but the main difference between the varieties is the swirl shape of 'Twister'.

TABLE 2

Comparison to known cultivar 'Laurentii'

| Characteristic | New Cultivar 'Twister' | Comparison Cultivar 'Laurentii' (unpatented) |
|---|---|---|
| Plant Vigor | Less vigorous plant with more leaves per plant | More vigor (65 cm aprox) with less leaves (2-4) |

TABLE 2-continued

Comparison to known cultivar 'Laurentii'

| Characteristic | New Cultivar 'Twister' | Comparison Cultivar 'Laurentii' (unpatented) |
|---|---|---|
| Color | Variegated leaves (irregular green cross-banding and yellowish green margins) | Variegated leaves (medium green cross-banding and yellowish green margins) |
| Shape | Wide and lanceolate leaves with swirl shape | Wide long and lanceolate leaves |
| Texture of leaves | smooth-textured leaves | smooth-textured leaves |

BRIEF DESCRIPTION OF THE PHOTOGRAPHS

The accompanying photographs illustrate the overall appearance of the new *Sansevieria* cultivar 'Twister' showing the colors as true as is reasonably possible with colored reproductions of this type. Colors in the photographs may differ slightly from the color value cited in the detailed botanical description which accurately describe the color of 'Twister'.

DETAILED BOTANICAL DESCRIPTION

Figure 1:
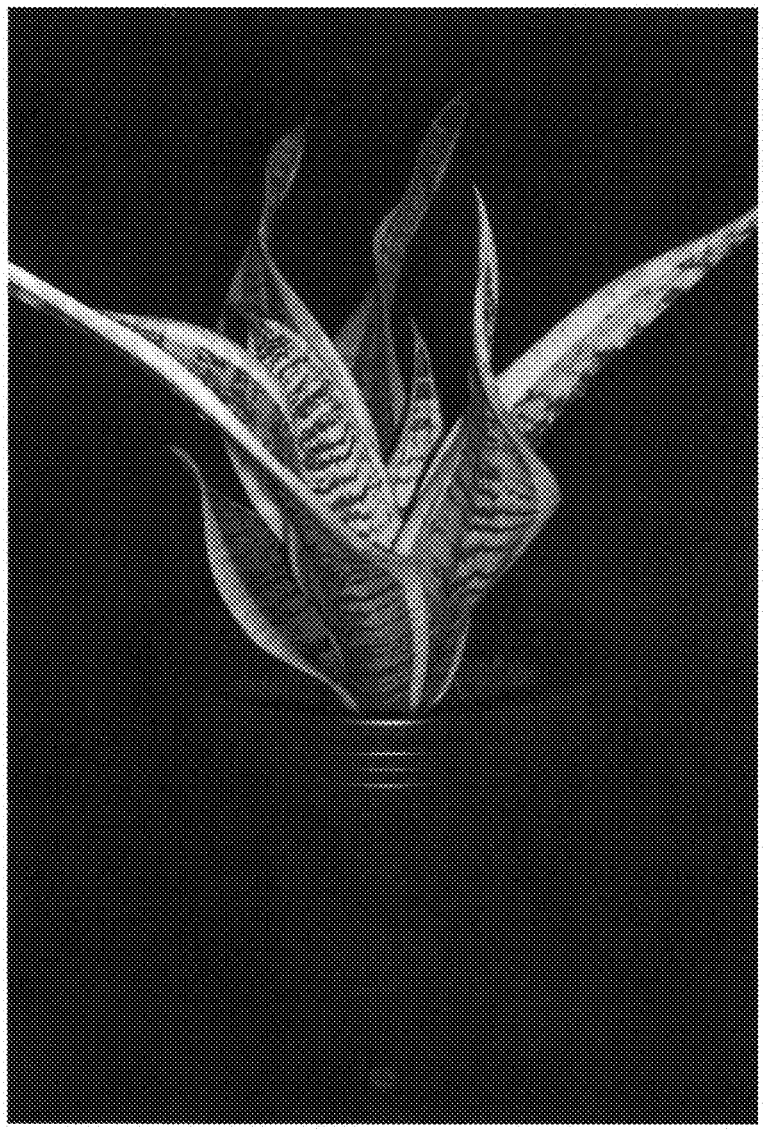
FIG. 1 Shows a side view of an eight-month old plant of *Sansevieria* 'Twister' in a 21 cm diameter pot.
Figure 2:
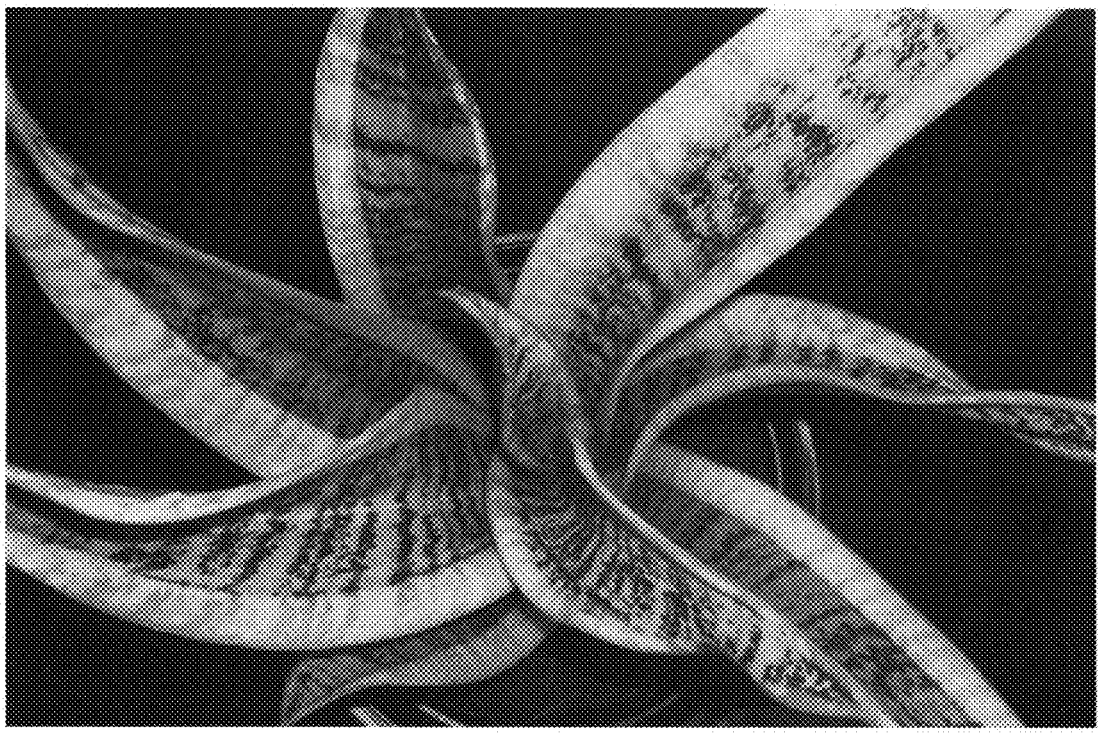
FIG. 2 Shows a top view of an eight-month old plant of *Sansevieria* 'Twister' in a 21 cm diameter pot .
Figure 3A:
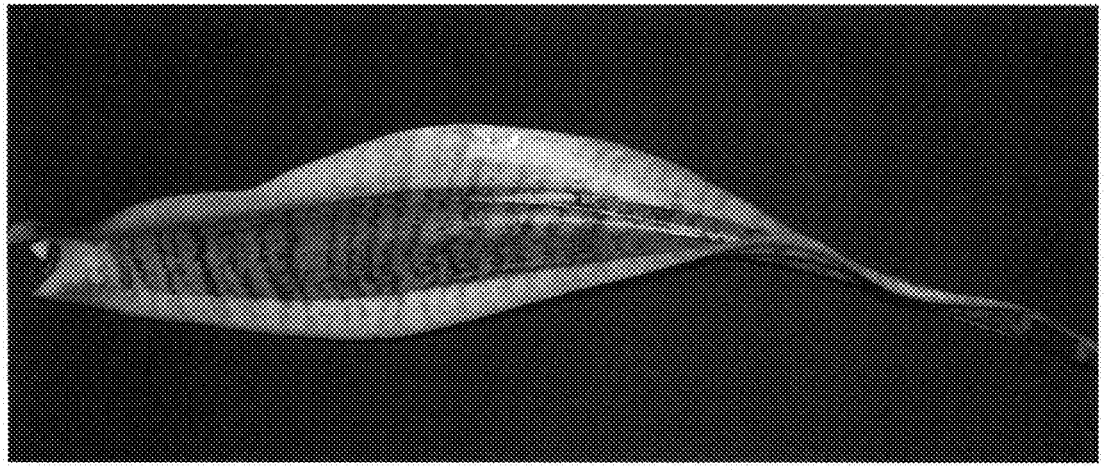
FIG. 3A Shows a close-up view of the upper side of a typical leaf of 'Twister' taken from an eight-month old plant.
Figure 3B:
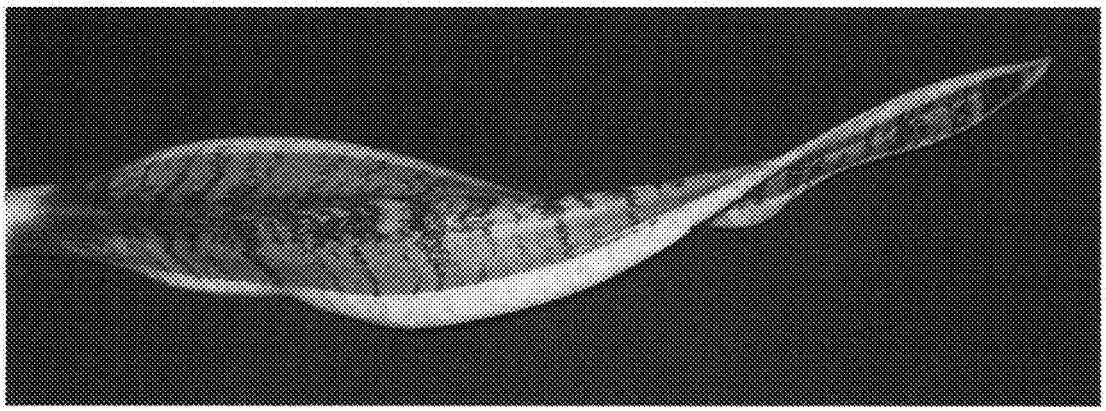
FIG. 3B Shows a close-up view of the under side of a typical leaf of 'Twister' taken from an eight-month old plant.

The new *Sansevieria* 'Twister' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'Twister' as grown in an open field in Monterrey, San Carlos de Alajuela province, Costa Rica, under conditions which closely approximate those generally used in commercial practice. Average temperature at Monterrey is 24.5° C. during the day and 18° C. at night. Plants grow under natural light conditions.

This crop does not require constant fertilization, however, to increase production per area about 200 kg $ha^{-1}$ N, 150 kg $ha^{-1}$ of P and 100 kg $ha^{-1}$ K are required. Production is closely related with soil conditions in which the plants are grown.

Color references are made to The Royal Horticultural Society Colour Chart (R.H.S. April 2009). The photographs and descriptions were taken during the rainy season in Monterrey, San Carlos, Alajuela province, Costa Rica when outdoor day temperature was 23° C. The age of the plants described is 8 months.

Classification:

*Botanical.*—*Sansevieria trifasciata.*

*Variety denomination.*—Twister.

Parentage: *Sansevieria trifasciata*, 'Black Gold Superba' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to a low temperature of about 12° C. and tolerant to a high temperature of about 35° C.

*Fertilization.*—200, 150 and 100 kg $ha^{-1}$ of N, P and K.

*Growth regulators.*—None.

Propagation:

*Type.*—Vegetative, by rooted cuttings.

*Rooting habit and description.*—Rhizomes, with short roots.

*Time to initiate roots.*—About 15 to 22 days at 18-25° C.

*Time to produce a rooted cutting.*—About 60 to 90 days at 18-25° C.

Plant:

*General appearance and form.*—Height: About 45 cm when grown in ground; About 35 cm when grown in a 21 cm size container. Spread: About 30 cm when grown in ground; About 25 cm when grown in 21 cm size container. Form: Monocot; leaf bases arranged in a rosette around growth point. Shape: inverted triangle.

*Growth rate and habit.*—About 2 cm per week; upright.

*Fragrance.*—None.

*Stem.*—Modified (Rhizome and foliage).

*Length.*—About 6 cm when grown in ground; About 5 cm when grown in 21 cm size container. Diameter: About 1.8 cm to 2 cm. Shape: round. Texture: rough. Color: RHS 17A. Strength: strong and durable. Internode length: About 0.3 mm to 0.7 mm.

Foliage:

*Quantity.*—About 7.

*Arrangement and attachment.*—Single, alternate; leaf bases arranged in a rosette around growth point.

*Leaf length.*—About 32 cm.

*Leaf width.*—About 5.5 cm.

*Overall shape of leaf.*—Lanceolate.

*Apex shape.*—Acute, triangular.

*Base shape.*—Plane.

*Margin.*—Sharp, smooth.

*Texture.*—Upper Surface: smooth and waxy. Under Surface: smooth and waxy.

*Pubescence.*—None.

*Color of mature leaf.*—Upper Surface: RHS 141A with bands of RHS 149B and RHS 149D and margins of RHS 154B and RHS 154D. Lower Surface: RHS 141A with bands of RHS 149B and RHS 149D and margins of RHS 154B and RHS 154D.

*Color of immature leaf.*—Upper Surface: bands of RHS 130D and 141A, with margins of 154B and 154D. Lower Surface: bands of RHS 130D and 141A, with margins of 154B and 154D. Venation: Pattern: longitudinal/parallel leaf shape.

*Leaf fragrance.*—None.

Inflorescence description:

*Arrangement and type.*—Inflorescence.

*Orientation at opening.*—Out of the spike.

*Quantity per plant with at least one open flower.*—One inflorescence per plant. About 22 at 2 weeks. About 22 flowers opened 2 weeks after appearance of the spike. Flowers sporadically and profusely under growth conditions.

*Inflorescence size.*—Length: About 28 cm. Diameter: About 4 cm.

*Flower size.*—Length: About 2 cm. Diameter: About 1 cm. Depth: About 1 cm.

*Fragrance.*—Soft and pleasant.

*Bud.*—Rate of opening: About 7 to 8 days, according to weather. Shape: ovoid. Length: About 2.0 cm. Diameter: About 3.0 mm. Color: Apex: RHS 150A. Base: RHS 142A. Texture (both surfaces): smooth.

Petals:

*Quantity.*—6.

*Arrangement.*—Star-shaped. No further data on the instant plant's petals was collected.

Reproductive organs:

*Androecium.*—Stamen: Number: 5 per flower. Length: About 1.3 cm. Color: RHS 150C. Anther: Length: About 2.0 mm. Width : About 1.0 mm. Color: RHS 150C. Filament: Length: About 1.1 cm. Color: RHS 150C. Pollen: Amount: moderate. Color: RHS 154D.

*Gynoecium.*—Pistil: Number: One per flower. Length: About 2.1 cm. Stigma: Length: About 6.0 mm. Width: About 0.8 mm. Color: RHS 150C. Style: Length: About 1.3 mm. Color: RHS 150C. Ovary: Length: About 3 mm. Width: About 2.5 mm. Color: RHS 150C.

Fruit: None observed.

Weather resistance: Moderately drought tolerant.

Disease/pest resistance: Not observed for disease/pest resistance.

Disease/pest susceptibility: Not observed for disease/pest susceptibility.

I claim:

1. A new and distinct variety of *Sansevieria* plant named 'Twister', substantially as illustrated and described herein.

* * * * *